United States Patent
Dong et al.

(10) Patent No.: US 12,186,272 B2
(45) Date of Patent: Jan. 7, 2025

(54) ORAL DRUG DELIVERY DEVICE

(71) Applicant: SHANGHAI WD PHARMACEUTICAL CO., LTD, Shanghai (CN)

(72) Inventors: Liang Chang Dong, Shanghai (CN); Yang Lei, Shanghai (CN); Gang Wu, Shanghai (CN); Yan Jiao, Shanghai (CN); Jingmin Shi, Shanghai (CN)

(73) Assignee: SHANGHAI WD PHARMACEUTICAL CO., LTD, Shanghai (CN)

( * ) Notice: Subject to any disclaimer, the term of this patent is extended or adjusted under 35 U.S.C. 154(b) by 742 days.

(21) Appl. No.: 17/420,618

(22) PCT Filed: Jan. 22, 2020

(86) PCT No.: PCT/CN2020/073865
§ 371 (c)(1),
(2) Date: Jul. 2, 2021

(87) PCT Pub. No.: WO2020/143843
PCT Pub. Date: Jul. 16, 2020

(65) Prior Publication Data
US 2022/0110832 A1    Apr. 14, 2022

(30) Foreign Application Priority Data
Jan. 7, 2019    (CN) .......................... 201910012935.4

(51) Int. Cl.
*A61J 7/00*    (2006.01)
*A61K 31/137*    (2006.01)
(Continued)

(52) U.S. Cl.
CPC ........... *A61J 7/0061* (2013.01); *A61K 31/137* (2013.01); *A61K 31/138* (2013.01);
(Continued)

(58) Field of Classification Search
CPC ............... A61J 3/07; A61J 3/071; A61J 3/072
See application file for complete search history.

(56) References Cited

U.S. PATENT DOCUMENTS 5,718,681 A *    2/1998    Manning .............. A47G 21/183
239/33
6,024,721 A    2/2000    Wong et al.
(Continued)

FOREIGN PATENT DOCUMENTS

CN    106793834 A    5/2017
CN    107441972 A    12/2017
(Continued)

OTHER PUBLICATIONS

Extended European Search Report dated Dec. 22, 2022 issued in European Application No. 20738987.5, 8 pages.
(Continued)

*Primary Examiner* — Dung T Ulsh
(74) *Attorney, Agent, or Firm* — FOLEY & LARDNER LLP

(57) ABSTRACT

Disclosed is an oral drug delivery device, comprising a tubular member, a drug holding part, a device cap and a turbulence-creating means. The tubular member has openings at both ends and an inner cavity; the opening at one end is a first opening and the opening at the other end is a second opening; the inner cavity communicates the first opening and the second opening. The turbulence-creating means comprises a step structure or a fold structure, and is disposed in the inner cavity and positioned between the second opening and the drug holding part. By using the oral drug delivery device of the present invention, turbulence can be generated during a normal sipping process, thereby providing ample mixing of drug-containing granules or multi-
(Continued)

particulates with drinkable liquids. Moreover, the device is telescopic, which reduces the size and is convenient to carry.

19 Claims, 5 Drawing Sheets

(51) Int. Cl.

| | | |
|---|---|---|
| *A61K 31/138* | (2006.01) | |
| *A61K 31/167* | (2006.01) | |
| *A61K 31/197* | (2006.01) | |
| *A61K 31/43* | (2006.01) | |
| *A61K 31/4402* | (2006.01) | |
| *A61K 31/4439* | (2006.01) | |
| *A61K 31/47* | (2006.01) | |
| *A61K 31/4748* | (2006.01) | |
| *A61K 31/7048* | (2006.01) | |

(52) U.S. Cl.
CPC .......... *A61K 31/167* (2013.01); *A61K 31/197* (2013.01); *A61K 31/43* (2013.01); *A61K 31/4402* (2013.01); *A61K 31/4439* (2013.01); *A61K 31/47* (2013.01); *A61K 31/4748* (2013.01); *A61K 31/7048* (2013.01)

(56) References Cited

U.S. PATENT DOCUMENTS

| | | |
|---|---|---|
| 6,096,003 A | 8/2000 | Wong et al. |
| 6,109,538 A | 8/2000 | Villani et al. |
| 6,210,713 B1 | 4/2001 | Wong et al. |
| 8,334,003 B2 | 12/2012 | Baron |
| 11,051,545 B2 | 7/2021 | Batista et al. |

FOREIGN PATENT DOCUMENTS

| | | | |
|---|---|---|---|
| CN | 108804803 A | 11/2018 | |
| CN | 110559185 A | 12/2019 | |
| CN | 111407663 A | 7/2020 | |
| DE | 10342514 A1 | 4/2005 | |
| EP | 0383503 A1 | 8/1990 | |
| EP | 1517628 B1 | 1/2008 | |
| WO | WO-03013977 A1 * | 2/2003 | ............ B65D 51/24 |
| WO | 2006012442 A2 | 2/2006 | |

OTHER PUBLICATIONS

Notice of Reasons for Refusal dated Oct. 4, 2022 issued in Japanese Application No. 2021-539676, with English translation, 6 pages.
International Search Report dated Apr. 14, 2020 issued in International Application No. PCT/CN2020/073865, with English translation, 5 pages.
Written Opinion of the International Searching Authority dated Apr. 14, 2020 issued in International Patent Application No. PCT/CN2020/073865, with English translation, 11 pages.

\* cited by examiner

Telescopic steps creating turbulence fold clusters creating turbulence

ORAL DRUG DELIVERY DEVICE

The present application is a 371 of PCT/CN2020/073865, filed Jan. 22, 2020, which is based upon and claims priority to Chinese Patent Application No. CN201910012935.4 filed on Jan. 7, 2019, the contents of which are incorporated herein by reference in their entirety.

TECHNICAL FIELD

The present disclosure relates to the field of medical equipment, specifically relates to an oral drug delivery device.

BACKGROUND

Tablets and capsules are the most convenient and most acceptable oral dosage forms. However, some patient populations, especially pediatric and geriatric ones, usually have difficulty in swallowing large size tablets and capsules. There are some patients who are reluctant to take the orally administered drug because of the perception of an unacceptable bad taste. Therefore, various drug delivery devices have been provided to facilitate the swallowing of large tablets and capsules and to minimize the perception of the administered dose for patients. The following patents and applications related to the sipping device are incorporated herein by reference.

EP 0383503 A1 describes an improved device for retaining and positioning a unit dosage form of a therapeutic agent in a tube, which is adapted to deliver the therapeutic agent with a flow of liquid drawn through the tube by normal sipping action of a patient. The device has a sieve, whose surface area greater than the luminal cross-sectional area of the tube, thereby minimizing resistance to the fluid flow during the sipping action.

U.S. Pat. No. 6,096,003 describes a sipping device that comprises an elongated tubular member with a deformable closure (equivalent to a one-way valve without creating turbulence), which is adapted to allow the delivery of an active agent upon deformation created by a normal sipping action.

U.S. Pat. No. 6,109,538 discloses a sipping device that comprises an elongated tube with a pair of sieves being disposed in the lumen of the tube to constrain a flavoring object, thereby imparting the flavor to drinkable liquids through the lumen of the tube.

EP 1517628 B1 describes a sipping device consisting of a straw, a removable or fixed plug and a cap for oral administration of vitamins and/or nutrient preparations that are at least partially soluble in drinkable liquids.

U.S. Pat. No. 6,210,713 B1 describes a sipping device that comprises an elongated tubular member with a one-way valve that serves as a closing device and allows passage of fluid through the one-way valve during a normal sipping action.

U.S. Pat. No. 8,334,003 describes a sipping device that comprises an elongated tubular member with a pair of filters at each end of the tubular member to retain the flavoring granules within the filter device, thereby allowing the flavoring granules to enter a plain beverage through normal sipping action.

U.S. Pat. No. 6,024,721 describes a sipping device that comprises an elongated tubular member with a mixing chamber, whose diameter is greater than the diameter of the tubular member to provide an improved mixing of drinkable liquids with an active agent in the device. However, such devices are difficult to practice and manufacture. In addition, the incorporation of a mixing chamber with an inner diameter greater than that of the tubular member into the sipping device will reduce the flow rate of drinkable liquids into the mouth through normal sipping action, thereby increasing the potential of perceiving the bad taste of the active agent.

CONTENT OF THE PRESENT INVENTION

In order to solve the technical problem that there is lack of a device for effectively promoting the drug swallowing in the prior art, the present invention provides an oral drug delivery device and a preparation method thereof.

One of the technical solutions of the present invention is to provide an oral drug delivery device comprising a tubular member, a drug holding part, a device cap and a turbulence-creating means, wherein the tubular member has openings at both ends and an inner cavity with a first opening at one end and a second opening at the other end, and the inner cavity communicates the first opening and the second opening; the drug holding part has a porous structure, which is retained in the inner cavity near the first opening for holding granules or multi-particulates containing active pharmaceutical ingredients; the porous structure has one or more orifices allowing the passage of liquid, and the orifices has a smaller diameter than the granules or multi-particulates containing the active pharmaceutical ingredients; the device cap is a detachable connection and is disposed outside the second opening; the turbulence-creating means comprises a step structure or a fold structure provided in the inner cavity and positioned between the second opening and the drug holding part.

When in use, the device cap is removed from the second opening; the first opening end is in contact with drinkable liquids; the second opening end is placed in the patient's mouth; the tubular member allows the passage of the drinkable liquids; the drug holding part is located inside the tubular member near the first opening end (i.e., the liquid end) to retain the drug in the form of granules or multi-particulates. Due to the function of the turbulence-creating means, turbulence may be created in the oral drug delivery device, thereby improving the mixing of drug-containing granules or multi-particulates with drinkable liquids.

A preferred embodiment provides an oral drug delivery device as described above, wherein the first opening has a diameter smaller than the minimum diameter of the drug holding part, thereby retaining the drug holding part in the inner cavity. In the present invention, since the drug holding part has a cylindrical or a truncated cone-like shape, the diameter of its cross section may be different. Therefore, the drug holding part may be retained in the inner cavity of the tubular member without using other fixing devices. When the drug holding part is matched with the tubular member, an inner cavity that may hold drug-containing granules or multi-particulates is formed. Thus, when sipping, drinkable liquids flow through the porous structure of the drug holding part through the first opening to reach the second opening. The diameter of the second opening may be set to be smaller than the maximum diameter of the drug holding part, so that when the device cap is not used to close the second opening, even if the drug holding part accidentally passes through the step structure or the fold structure, it may be retained in the inner cavity without falling out.

A preferred embodiment provides an oral drug delivery device as described above, wherein the tubular member has at least two tubular segments which are connected to each other hermetically and can be elongated or shorten axially along the tubular member; when the tubular member is elongated, a turbulence-creating means with at least one step structure is formed. The turbulence-creating means may form a step structure because, for example, the inner diameters of adjacent tubular segments are different in the cross-sectional direction. More specifically, the height of the step is determined by the thickness of the tubular segment with the smaller inner diameter among the two adjacent tubular segments connected by the telescopic nesting. Within the practical range, the greater the number of step structures, the greater the Reynolds number of created turbulences; within the reasonable range, the greater the height of the step structure, the greater the Reynolds number of created turbulences. In the present invention, the tubular segments connected by the telescopic nesting of the oral drug delivery device is similar to the sleeve configuration of a telescope, so it is also called telescope-type configuration or telescope-type telescopic sleeve configuration. The axial elongating or shortening of the tubular member may be a sleeve-type elongating or shortening, or any other elongating or shortening realized by, for example, rotation.

A more preferred embodiment provides an oral drug delivery device as described above, wherein the number of the tubular segments is 2-5; preferably 2-4; most preferably 3.

A more preferred embodiment provides an oral drug delivery device as described above, wherein when the number of the tubular segments is three: in the direction from the first opening to the second opening, the inner diameter of the first tubular segment is the same as the inner diameter of the third tubular segment, and the outer diameter of the second tubular segment is smaller than the inner diameter of the first tubular segment, and each tubular segment can be elongated or shorten axially along the other tubular segments; or, the inner diameter of the first tubular segment, the outer diameter of the second tubular segment, the inner diameter of the second tubular segment and the outer diameter of the third tubular segment gradually decrease in the direction from the first opening to the second opening, and each tubular segment can be elongated or shorten axially along the other tubular segments. Since the edge lines of the three tubular segments on the profile are parallel to each other, the adjacent tubular segments can be elongated or shorten axially.

When the number of the tubular segments is four: in the direction from the first opening to the second opening, the inner diameter of the first tubular segment is the same as the inner diameter of the third tubular segment, and the inner diameter of the second tubular segment is the same as the inner diameter of the fourth tubular segment, wherein the inner diameter of the second tubular segment is smaller than the first tubular segment, and each tubular segment can be elongated or shorten axially along the other tubular segments; or, the inner diameters of the first tubular segment to the fourth tubular segment in the direction from the first opening to the second opening gradually decrease, and each tubular segment can be elongated or shorten axially along the other tubular segments. Since the sidelines of three tubular segments in the longitudinal section are parallel to each other, the adjacent tubular segments can be elongated or shorten axially. The situation where the number of tubular segments is greater than four may be deduced from the above analogy.

A more preferred embodiment provides an oral drug delivery device as described above, wherein the tubular member has at least one fold structure with a pair of wing parts and a turning end; the fold structure can be elongated or shorten axially along the tubular member, and forming a turbulence-creating means when the tubular member is elongated. The turning end is the crimped part of the fold structure from one wing part to the other wing part. In the cross section, the turning end is usually a point, so a pair of wing parts and a turning end usually form the structure of an angle. The angle may be an acute angle, a right angle or an obtuse angle.

When the tubular member includes a plurality of successive fold structures to form a fold cluster configuration, the fold cluster configuration is similar to an accordion-type configuration, therefore, in the present invention, the fold cluster configuration is also called an accordion-type configuration or an accordion-type fold configuration. A more preferred embodiment provides an oral drug delivery device as described above, wherein a plurality of successive fold structures forms a fold cluster configuration having a number of 1-5; preferably 2-3.

A more preferred embodiment provides an oral drug delivery device as described above, wherein the cross-sectional diameter of the inner cavity at the fold structure is smaller than that of the inner cavity at the junction of the tubular member and the fold structure, in addition, the minimum inner diameter of the cavity section at the fold structure is not less than one-fifth of the cross-sectional diameter of the inner cavity of the tubular member. At this time, the turning end of the fold structure forms a protrusion toward the axial direction of the tubular member, so that a turbulence-creating means may already be formed when the oral drug delivery device is in a shorten form.

A preferred embodiment provides an oral drug delivery device as described above, wherein the tubular member has a maximum outer diameter of 4.0-15.0 mm and a minimum inner diameter of 2.0-14.8 mm; and/or, the length of the tubular member is 5-30 cm in a shorten form and 10-50 cm in an elongated form.

The active pharmaceutical ingredient may be prepared with other excipients into granules or multi-particulates through a certain process, if the drugs incorporated into the granules or multi-particulates do not taste good, they may need to be coated with taste masking compositions. Multi-particulates may also be coated with enteric coating or extended-release coating, or enteric coating and extended-release coating, respectively, for extended or delayed release or enteric/extended-release. Therefore, a more preferred embodiment provides an oral drug delivery device as described above, when the drug holding part comprises granules or multi-particulates containing active pharmaceutical ingredients, the granules or multi-particulates has a diameter of 50-5000 μm, preferably 75-2000 μm, and more preferably 100-1000 μm; the active pharmaceutical ingredients include, but are not limited to one or more of the following: dabigatran etexilate or pharmaceutically acceptable salt thereof, levodopa/carbidopa, montelukast, lansoprazole, omeprazole, amoxicillin, clarithromycin, acetaminophen, dextromethorphan, doxylamine, pseudoephedrine and diphenhydramine.

In a preferred embodiment, the oral drug delivery device contains granules or multi-particulates comprising 9-48 wt % of dabigatran etexilate mesylate and 9-44 wt % of Soluplus®, 0-30 wt % of Kolliphor P407, 0-23 wt % of Kolliphor P188, 0-58 wt % of lactose monohydrate, 0-32 wt % of mannitol, 0-20 wt % of cross-linked carboxymethylcellulose sodium, 0-5 wt % of silicon dioxide and 0-3 wt % of magnesium stearate. Preferably, the granules or multi-particulates comprise 10.4-17.2 wt % of dabigatran etexilate mesylate, 24.3-35.7 wt % of Soluplus®, 13.1 wt % of Kolliphor P407 or 19.0 wt % of Kolliphor P188, 0-52.2 wt % of lactose monohydrate, 0-17.9 wt % of mannitol, 0-9.7 wt % of cross-linked carboxymethylcellulose sodium and 0-0.5 wt % of magnesium stearate.

In a specific embodiment, the oral drug delivery device contains multi-particulates comprising 10.4 wt % of dabigatran etexilate mesylate, 2.6 wt % of Soluplus®, 13.1 wt % of Kolliphor P407, 52.2 wt % of sucrose core and 21.7 wt % of Soluplus powder. The multi-particulates are preferably in doses of 50 mg and 75 mg of active pharmaceutical ingredient.

In a specific embodiment, the oral drug delivery device contains granules comprising 17.2 wt % of dabigatran etexilate mesylate, 35.7 wt % of Soluplus®, 17.9 wt % of mannitol, 19.0 wt % of Kolliphor P188, 9.7 wt % of cross-linked carboxymethylcellulose sodium and 0.5 wt % of magnesium stearate. The granules are preferably in doses of 50 mg and 75 mg of active pharmaceutical ingredient.

In a preferred embodiment, the oral drug delivery device contains granules and multi-particulates comprising 42.3-70.41 wt % of levodopa, 0-45.7 wt % of carbidopa monohydrate, 1.9-3.81 wt % of sodium dodecyl sulfate, 4.8-19.03 wt % of fillers (such as one or more of microcrystalline cellulose, hydroxypropyl cellulose and mannitol), 1.9-4.8 wt % of binding agent (such as one or more of methylcellulose, hypromellose, hydroxypropyl cellulose, sodium carboxymethyl cellulose, povidone and gelatin). Preferably, the multi-particulates further contain a coating membrane comprising cellulose acetate and copovidone, and the cellulose acetate accounts for 50-90 wt % of the coating membrane; the copovidone accounts for 10-50 wt % of the coating membrane.

In a preferred embodiment, the oral drug delivery device contains granules and multi-particulates, wherein the granules are immediate-release granules, the multi-particulates are extended-release multi-particulates, and the granules contain 42.3 wt % of levodopa, 45.7 wt % of carbidopa monohydrate, 1.9 wt % of sodium dodecyl sulfate, 4.8 wt % of hydroxypropyl methylcellulose (HPMC) E5, 4.8 wt % of cross-linked carboxymethylcellulose sodium and 0.5 wt % of magnesium stearate; and/or, the multi-particulates contains 70.41 wt % of levodopa, 19.03 wt % of microcrystalline cellulose, 3.81 wt % of sodium dodecyl sulfate, 1.90 wt % of Povidone K29/32, 4.12 wt % of cellulose acetate 39.8 and 0.73 wt % of Copovidon (Kollidone VA64). Preferably, the coating level of the extended-release multi-particulates is 5.1-10.9 wt %, preferably 7.7%. More preferably, the extended-release multi-particulates are coated with enteric-soluble compositions at a coating level of 3-10 wt %.

In a preferred embodiment, the oral drug delivery device contains granules comprising 0.83 wt % of montelukast sodium, 93.67 wt % of mannitol, 5.00 wt % of hydroxypropyl cellulose and 0.50 wt % of magnesium stearate. The granules are preferably 500 mg (4 mg montelukast), 625 mg (5 mg montelukast), 1250 mg (10 mg montelukast) and 500 mg (10 mg montelukast).

In a preferred embodiment, the oral drug delivery device contains granules and multi-particulates, wherein the granules are amoxicillin granules and clarithromycin granules, and the multi-particulates are lansoprazole delayed-release multi-particulates, the filling weights of the lansoprazole delayed-release multi-particulates, amoxicillin granules and clarithromycin granules are 480 mg, 1334 mg and 840 mg, respectively. The lansoprazole delayed-release multi-particulates comprise a core and an enteric coating, the core contains 6.3 wt % of lansoprazole, 31.3 wt % of sugar pellets, 11.3 wt % of corn starch, 12.1 wt % of sucrose, 1.3 wt % of low-substituted hydroxypropyl cellulose, 0.8 wt % of hydroxypropyl cellulose and 6.3 wt % of magnesium carbonate, the enteric coating contains 13.1 wt % of Eudragit L-30D solid component, 4.0 wt % of talcum powder, 1.3 wt % of PEG 6000, 0.7 wt % of Tween 80 and 1.8 wt % of titanium dioxide. The amoxicillin granules contain 75.0 wt % of amoxicillin trihydrate, 24.5 wt % of microcrystalline cellulose, and 0.5 wt % of magnesium stearate. The clarithromycin granules contain 59.5 wt % of clarithromycin, 30.0 wt % of microcrystalline cellulose, 5.0 wt % of cross-linked carboxymethylcellulose sodium, 5.0 wt % of Povidone, and 0.5 wt % of magnesium stearate.

In a preferred embodiment, the oral drug delivery device contains granules and multi-particulates, wherein the granules are amoxicillin granules and clarithromycin granules, the multi-particulates are omeprazole delayed release multi-particulates, and the filling weights of the omeprazole delayed-release multi-particulates, amoxicillin granules and clarithromycin granules are 320 mg, 1334 mg and 840 mg, respectively. The omeprazole delayed-release multi-particulates comprise a core and an enteric coating, the core contains 6.3 wt % of omeprazole, 31.3 wt % of sugar pellets, 11.3 wt % of corn starch, 12.1 wt % of sucrose, 11.3 wt % of low-substituted hydroxypropyl cellulose, 0.8 wt % of hydroxypropyl cellulose and 6.3 wt % of magnesium carbonate, the enteric coating contains 13.1 wt % of Eudragit L-30D solid component, 4.0 wt % of talcum powder, 1.3 wt % of PEG 6000, 0.7 wt % of Tween 80 and 1.8 wt % of titanium dioxide. The amoxicillin granules contain 75.0 wt % of amoxicillin trihydrate, 24.5 wt % of microcrystalline cellulose, and 0.5 wt % of magnesium stearate. The clarithromycin granules contain 59.5 wt % of clarithromycin, 30.0 wt % of microcrystalline cellulose, 5.0 wt % of cross-linked carboxymethylcellulose sodium, 5.0 wt % of Povidone, and 0.5 wt % of magnesium stearate.

In a preferred embodiment, the oral drug delivery device contains granules, and the active pharmaceutical ingredients of the granules are acetaminophen, dextromethorphan, doxylamine, pseudoephedrine and diphenhydramine, the dosage ranges of the active pharmaceutical ingredients are respectively 250-1000 mg, 10-30 mg, 6.25-12.5 mg, 20-30 mg and 12.5-25 mg.

Drinkable liquids may be used to carry drug-containing granules or multi-particulates through the tubular part of the device by normal sipping action. The liquid is preferably any drinkable liquid, including but not limited to water, lemonade, pulp free juice, milk, soda, coffee and tea.

One of the technical solutions of the present invention is to provide a method for preparing an oral drug delivery device comprising the following steps:
1) preparing the turbulence-creating means and assembling it with the tubular member;
2) preparing the drug holding part and retaining it in the inner cavity near the first opening;
3) setting the device cap at the second opening.

Preferably, the step of filling the drug is further included before the step 3).

On the basis of conforming to common knowledge in the art, the above-mentioned preferred conditions can be arbitrarily combined to obtain each preferred embodiment of the present invention.

The reagents and raw materials used in the present invention are all commercially available.

Advantageous effects of the present invention are that by using the oral drug delivery device of the present invention, ample mixing of drug-containing granules or multi-particulates with drinkable liquids for normal sipping action is provided; moreover, the device is telescopic, which reduces the size and is convenient to carry. In addition, the granules or multi-particulates containing drugs whose active ingredient is dabigatran etexilate showed significantly faster dissolution at acidic pH and less precipitation at neutral pH. At the same time, the preparation method of the oral drug delivery device of the present invention is simple, and the application effect is good.

BRIEF DESCRIPTION OF THE DRAWINGS

FIG. 1A. in a shorten form, FIG. 1B. in an elongated form prior to sipping action, FIG. 1C. in an elongated form during sipping action;

FIG. 2A. in a shorten form, FIG. 2B. in an elongated form prior to sipping action, FIG. 2C. in an elongated form during sipping action;

FIG. 3A. in a shorten form, FIG. 3B. in an elongated form prior to sipping action, FIG. 3C. in an elongated form during sipping action;

FIG. 4A. turbulence formed by the oral drug delivery device of the present invention including a turbulence-creating means with a step structure; FIG. 4B. turbulence formed by the oral drug delivery device of the present invention including a turbulence-creating means with a fold structure;

DESCRIPTION OF REFERENCE SIGNS IN THE DRAWINGS

Figure 1A:
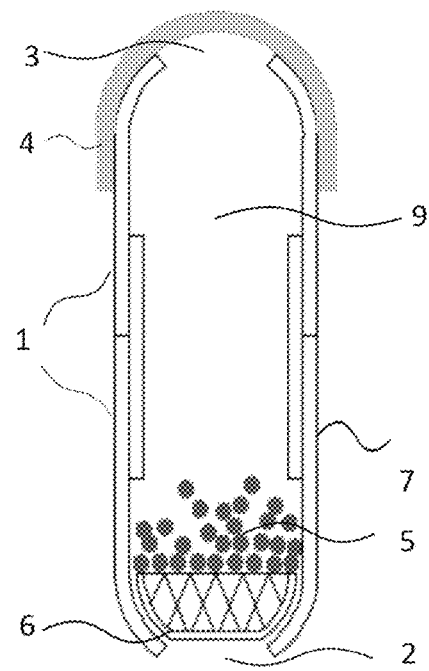
FIG. 1A to FIG. 1C are schematic diagrams of an oral drug delivery device including a turbulence-creating means with a step structure, type I.

1: tubular member
11: first tubular segment
12: second tubular segment
13: third tubular segment
2: first opening
21: inward crimp of the first opening
3: second opening
31: inward crimp of the second opening
4: device cap
5: granules or multi-particulates containing active pharmaceutical ingredients
6: drug holding part
61: orifice
7: step structure
71: first step
71: second step
8: fold cluster
81: first fold cluster
811: fold structure
82: second fold cluster
9: inner cavity

DETAILED DESCRIPTION OF THE PREFERRED EMBODIMENT

The following examples of the present invention will be illustrated with reference to the drawings. In the drawings of the description, elements with similar structures or functions will be represented by the same element symbols. It is understood that the drawings are only used to facilitate the description of the embodiments of the present invention, and are not intended to be an exhaustive description of the present invention nor to limit the scope of the present invention.

Figure 1B:
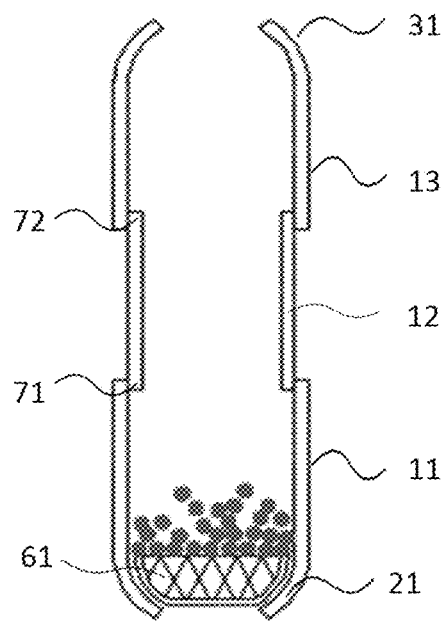
Figure 1C:
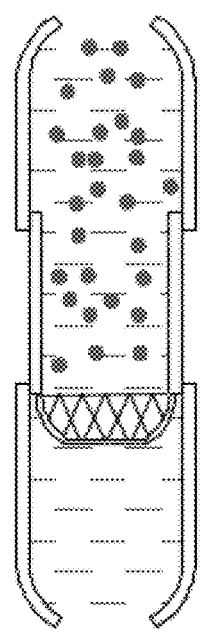
Figure 2A:
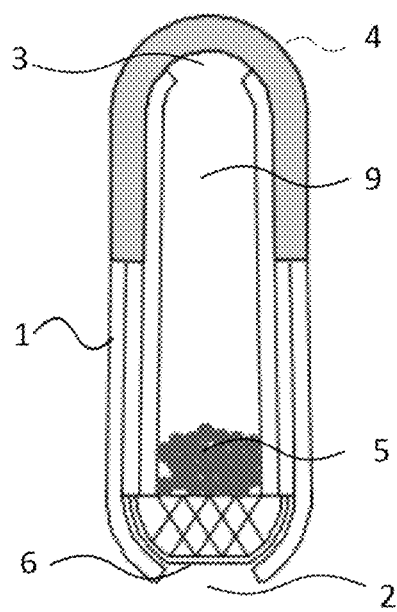
FIG. 2A to FIG. 2C are schematic diagrams of an oral drug delivery device including a turbulence-creating means with a step structure, type II.
Figure 2B:
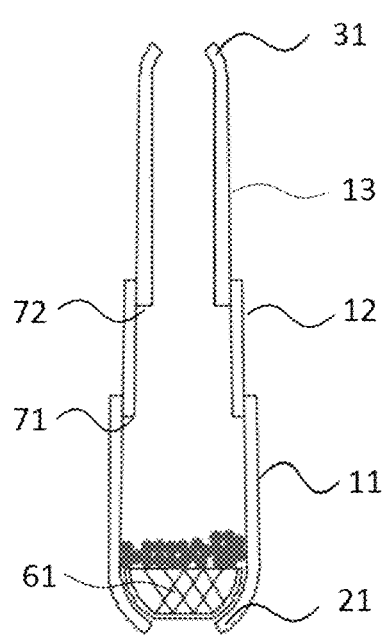
Figure 2C:
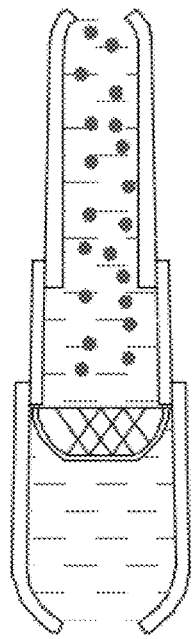

An oral drug delivery device including a turbulence-creating means having a step structure is prepared in the present invention. FIG. 1A to FIG. 2C respectively show a cross-sectional view of the type I and type II telescopic configuration of the oral drug delivery device according to the present invention. The oral drug delivery device is in a shorten form prior to use (FIG. 1A or FIG. 2A) and in an elongated form prior to sipping action (FIG. 1B or FIG. 2B), and granules are suspended during the sipping process (FIG. 1C or FIG. 2C). The oral drug delivery device shown in FIG. 1A to FIG. 2C comprises a tubular member 1 that can be elongated or shorten having a first opening 2, a second opening 3 and a device cap 4. FIG. 1A to FIG. 2C illustrate a tubular member composed of three tubular segments 11, 12, and 13, respectively. In FIG. 1A to FIG. 1C, in the direction from the first opening 2 to the second opening 3, the inner diameter of the first tubular segment 11 is the same as that of the third tubular segment 13, and the outer diameter of the second tubular segment 12 is smaller than the inner diameter of the first tubular segment 11, so that the first tubular segment 11 and the third tubular segment 13 can be elongated (FIG. 1B and FIG. 1C) or shorten (FIG. 1A) axially along the second tubular segment 12. In FIG. 2A to FIG. 2C, the inner diameter of the first tubular segment 11, the outer diameter and inner diameter of the second tubular segment 12, and the outer diameter of the third tubular segment 13 in the direction from the first opening 2 to the second opening 3 gradually decrease, however, the edge lines on the same side of the profile of the three tubular segments are parallel to each other, so that the third tubular segment 13 and the second tubular segment 12 can be elongated (FIG. 2B and FIG. 2C) or shorten (FIG. 2A) axially along the first tubular segment 11.

The drug holding part 6 is arranged in the inner cavity 9 of the tubular member 1 near the first opening 2, and the structure when it contains granules or multi-particulates 5 is showed in the figure. After the drug holding part 6 is placed in the inner cavity, the end of the first opening 2 is an inward crimp 21, so that the diameter of the opening after inwardly crimped is smaller than the minimum diameter of the structure of the drug holding part 6; the end of the second opening 3 is an inward crimp 31, so that the diameter of the opening after inwardly crimped is smaller than the maximum diameter of the structure of the drug holding part 6, thereby retaining the drug holding part 6 in the inner cavity. And a device cap 4 is arranged outside the second opening 3. The drug holding part 6 is matched with the tubular member 1 to form a space 5 that can contain the drug (in the example of the present invention, it appears as granules and multi-particulates structure, and the active ingredient of the drugs is contained in the granules and multi-particulates structure). The drug holding part 6 comprises a porous structure having a plurality of orifices 61, whose diameter is smaller than the granules or multi-particulates 5, allowing the passage of drinkable liquids; but when no liquid passes through, the granules or multi-particulates 5 remain in the inner cavity 9 of the tubular member 1. The oral drug delivery device is elongated to form a step structure 7, which is shown in FIG. 1A to FIG. 2C, and the step structure is arranged in the position of the inner cavity 9 between the second opening 3 and the drug holding part 6. The step structure 7 shown in FIG. 1A to FIG. 2C has a first step 71 and a second step 72, by sipping action, drinkable liquids pass through the steps 71 and 72 to create turbulence, thereby enhancing the mixing of drug-containing granules or multi-particulates 5 with drinkable liquids. It is well known to those skilled in the art that when the number of tubular segments increases, the total number of the step structures also increases accordingly, so the Reynolds number of created turbulences is also greater; in addition, when the height of the step structure increases in the range of the conventional art, the Reynolds number of created turbulences is also greater.

Figure 3A:
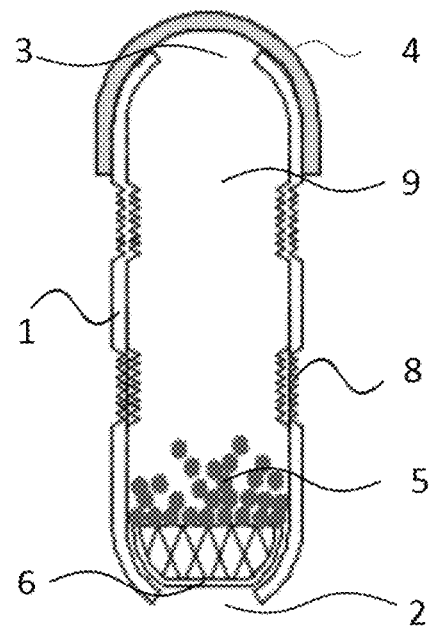
FIG. 3A to FIG. 3C are schematic diagrams of an oral drug delivery device including a turbulence-creating means with a fold structure.
Figure 3B:
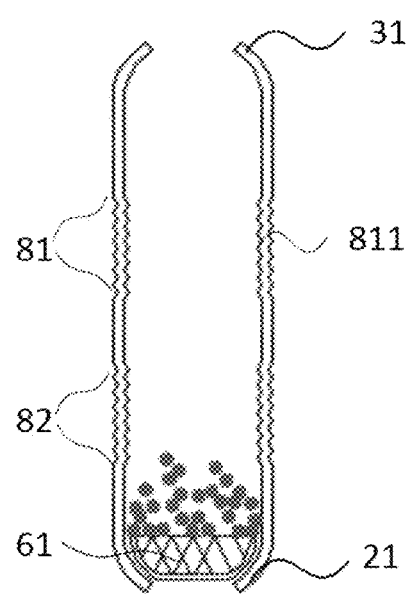
Figure 3C:
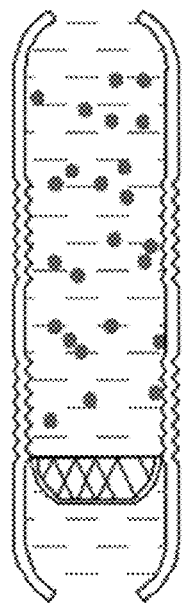

An oral drug delivery device including a turbulence-creating means with a fold structure is also prepared in the present invention. FIG. 3A to FIG. 3C show a cross-sectional view of the accordion-type fold cluster configuration of the oral drug delivery device according to the present invention. The device is in a shorten form prior to use (FIG. 3A) and in an elongated form prior to sipping action (FIG. 3B), and granules are suspended during the sipping process (FIG. 3C). The oral drug delivery device shown in FIG. 3A to FIG. 3C comprises tubular member 1 that can be elongated with an inner cavity 9 and a plurality of fold cluster configurations, two fold cluster configurations 81 and 82 are shown in FIG. 3A to FIG. 3C. Each fold cluster configuration has a plurality of fold structures 811. The oral drug delivery device comprises a first opening 2, a second opening 3 and a device cap 4. Contained in the inner cavity 9 of the tubular member are granules or multi-particulates containing active pharmaceutical ingredients 5 and a drug holding part 6. After the drug holding part 6 is placed in the inner cavity, the end of the first opening 2 is inwardly crimped, so that the diameter of the opening after inwardly crimped is smaller than the minimum diameter of the drug holding part 6; the end of the second opening 3 is inwardly crimped 31, so that the diameter of the opening after inwardly crimped is smaller than the maximum diameter of the structure of the drug holding part 6, thereby retaining the drug holding part 6 in the inner cavity. In addition, a device cap 4 is arranged outside the second opening 3. The drug holding part 6 shown in FIG. 3A to FIG. 3C is a porous structure, which has a plurality of orifices 61 and is positioned in the inner cavity 9 of the tubular member near the first opening 2. The drug holding part 6 is matched with the tubular member 1 to form a space that can contain the drug granules or multi-particulates containing active pharmaceutical ingredients 5. The diameter of orifices 61 of the porous structure is smaller than that of the granules or multi-particulates 5, thereby allowing the passage of drinkable liquids; but when there is no liquid passed through, the granules or multi-particulates 5 remain in the inner cavity 9 of the tubular member 1. When the oral drug delivery device is in an elongated form, drinkable liquids flow through the fold structure 811 to create turbulence through the sipping action, thereby enhancing the mixing of granules or multi-particulates containing active pharmaceutical ingredients 5 with drinkable liquids. It is well known to those skilled in the art that when the number of fold clusters increases, the total number of the fold structure also increases accordingly, so the Reynolds number of created turbulences is also greater; in addition, when the height of the protrusion of the fold structure toward the inner cavity increases in the range of the conventional art, the Reynolds number of created turbulences is also greater.

It is well known to those skilled in the art that after the drug holding part 6 is placed in the inner cavity 9 through the first opening 2 end, the device cap 4 can be directly disposed outside the second opening 3. At this time, because the device cap is connected to the second opening hermetically, even if the end of the second opening 3 is not inwardly crimped, due to the existence of the step structure or the fold structure, the drug holding part 6 will not reach the outside of the second opening 3 through the cavity 9, thereby retaining the drug holding part 6 in the inner cavity 9. At this time, if the end of the second opening 3 is inwardly crimped, the diameter of the opening after inwardly crimped is smaller than the maximum diameter of the drug holding part, which can further ensure that the drug holding part 6 will not be sipped into the patient's mouth, leading to medical accidents during the use of the oral drug delivery device.

Figure 4A:
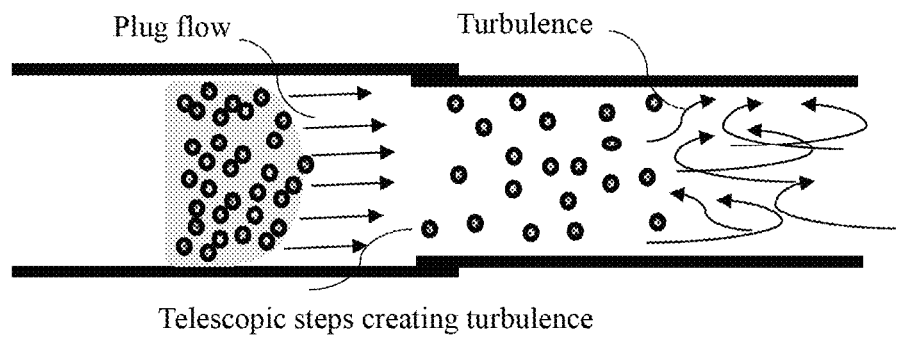
FIG. 4A to FIG. 4B are schematic diagrams of the plug flow and turbulence.
Figure 4B:
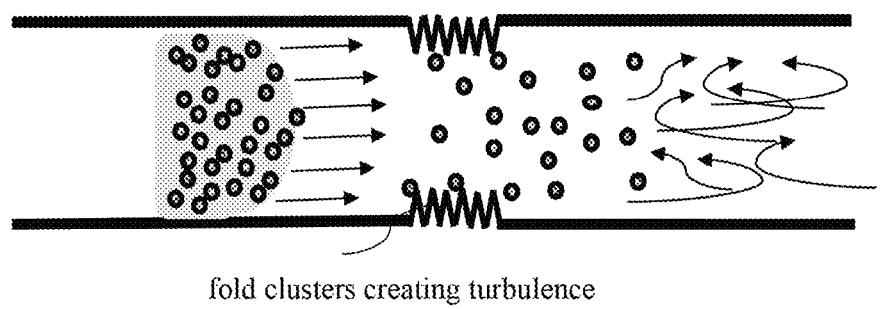

FIG. 4A to FIG. 4B schematically shows the plug flow and turbulence created by the oral drug delivery device including a turbulence-creating means with a step structure or a fold structure according to the present invention.

In the present invention, the tubular member 1 of the oral drug delivery device generally has an outer diameter between 4.0 mm and 15.0 mm. The inner cavity 9 of the tubular member 1 has a diameter usually between 2.0 mm and 14.8 mm. The length of the tubular member 1 is between 5 cm and 15 cm in its prepared form, and between 10 cm and 30 cm in its elongated form.

The preferred materials for manufacturing the tubular member 1, the drug holding part 6 and the device cap 4 are polypropylene and polyolefin family polymers conventional in the art.

The active pharmaceutical ingredients (API) covered by the present invention include, but are not limited to, dabigatran etexilate or pharmaceutically acceptable salt thereof, levodopa/carbidopa, montelukast, lansoprazole, omeprazole, amoxicillin, clarithromycin, acetaminophen, dextromethorphan, doxylamine, pseudoephedrine and diphenhydramine.

In an embodiment, an oral drug delivery device comprises dabigatran etexilate methylate (DEM) with enhanced solubility in the form of granules, which is prepared by using a hot melt granulation process.

In another embodiment, an oral drug delivery device comprises dabigatran etexilate methylate (DEM) with enhanced solubility in the form of multi-particulates, the DEM is prepared by using a spraying process.

In another embodiment, an oral drug delivery device comprises an extended-release levodopa/carbidopa formulation in the form of multi-particulates, which is prepared by using extrusion, spheronization, and coating processes.

In another embodiment of the present invention, an oral administration delivery device comprises montelukast granules, which are prepared by conventional granulation process, including wet granulation, fluidized bed granulation, dry granulation, and the like.

In another embodiment of the present invention, an oral administration delivery device comprises lansoprazole in the form of multi-particulates and amoxicillin and clarithromycin in the form of granules, the multi-particulates are prepared by spraying and coating processes, and the granules are prepared by conventional granulation process, including wet granulation, fluidized bed granulation, dry granulation, and the like.

In another embodiment of the present invention, an oral administration delivery device comprises omeprazole in the form of multi-particulates and amoxicillin and clarithromycin in the form of granules, the multi-particulates are prepared by spraying and coating processes, and the granules are prepared by conventional granulation process, including wet granulation, fluidized bed granulation, dry granulation, and the like.

In another embodiment of the present invention, an oral administration delivery device comprises cold drug granules prepared by conventional granulation process, including wet granulation, fluidized bed granulation, dry granulation, and the like.

One of the oral drug delivery devices in the present invention is an oral drug delivery device including a turbulence-creating means with a stepped structure. One configuration of the device may be manufactured by the following manufacturing steps. First, a three-part tubular member (type I or type II, see FIG. 1A and FIG. 2A) is manufactured by the traditional method of manufacturing straws.

Next, the drug holding part 6 is inserted into the first opening 2 end of the tubular member 1. Then, the end is inwardly crimped so that the drug holding part 6 can be retained in the inner cavity 9 of the tubular member 1. After that, the granules or multi-particulates containing active pharmaceutical ingredients 5 are filled into the tubular member 1 through the second opening 3 end of the tubular member 1. Finally, the filled tubular member 1 is enclosed by the device cap 4 and wrapped with an aluminum pouch (not shown in figures).

Another oral drug delivery device in the present invention is an oral drug delivery device including a turbulence-creating means with a fold structure. The device may be manufactured by the following manufacturing steps. First, the tubular member 1 with three sets of accordion-type fold configurations 8 is manufactured by the traditional process of manufacturing straws. Next, the drug holding part 6 is inserted into the first opening 2 end of the tubular member 1. Then, the end of the first opening 2 is inwardly crimped so that the drug holding part 6 can be retained in the inner cavity 9 of the tubular member 1. After that, the granules or multi-particulates containing active pharmaceutical ingredients 5 are filled into the tubular member 1 through the second opening 3 end of the tubular member 1. Finally, the filled tubular member 1 is enclosed by the device cap 4 and wrapped with an aluminum pouch (not shown in figures).

The present invention is further explained by specific embodiments below, but the present invention is not limited to the scope of the described embodiments. In the following examples, the experimental methods not specified in the following embodiments shall be selected in accordance with the conventional methods and conditions or in accordance with the product specifications.

EXAMPLE 1

Multi-particulates containing dabigatran etexilate mesylate (DEM) were prepared by spraying the solid solution/dispersion composition onto sugar pellets. The composition comprises, in weight percentage, 40% of dabigatran etexilate mesylate (DEM), 10% of polyethylene caprolactam-polyvinyl acetate-polyethylene glycol-grafted copolymer, Soluplus, and 50% of polyoxyethylene polyoxypropylene ether block copolymer, Kolliphor P407. First, these solid components were dissolved in 92% ethanol to prepare a coating solution with 24.2% of solid content. Then, 714.8 g of the coating solution containing 173.0 g of solid components was sprayed onto 346.0 g of pre-dried sugar cores by using a fluidized bed granulator with Wurster insert under appropriate air inlet pressure and at 38-40° C. of air inlet temperature. During the coating process, the spraying speed and atomization pressure were adjusted to keep the product temperature at 28-30° C. After the coating solution was exhausted, the coated pills were dried in a fluidized bed until the water content was below 1.7%. The target weight ratio of the drug layer to the sucrose core was 0.5:1.0. Additional Soluplus granules (180 mg) were added in the form of powder (<80 mesh). The Soluplus powder used in this experiment was obtained by grinding Soluplus granules, followed by sieving them with an 80-mesh sieve.

The DEM comprising multi-particulates (552.4 mg for 50 mg dose and 648.6 mg for 75 mg dose) and Soluplus powder (120 mg for 50 mg dose and 180 mg for 75 mg dose) were filled into the inwardly crimped first opening 2 end of the tubular member 1 through the second opening 3 end. Finally, the filled tubular member was enclosed by a device cap and wrapped with an aluminum pouch (not shown in figures). The compositions of the multi-particulates fill formulation in the device were listed in the Table 1.

TABLE 1

The compositions of the multi-particulates fill formulation in Example 1

| Compositions | wt % | wt/piece, mg (50 mg dose) | wt/piece, mg (75 mg dose) |
|---|---|---|---|
| Dabigatran etexilate mesylate (DEM)* | 10.4 | 57.7 | 86.5 |
| Soluplus | 2.6 | 14.4 | 21.6 |
| Kolliphor P407 | 13.1 | 72.1 | 108.1 |
| Sucrose core | 52.2 | 288.2 | 432.4 |
| Soluplus powder | 21.7 | 120.0 | 180.0 |
| Total content | 100.0 | 552.4 | 828.6 |

*57.7 mg and 86.5 mg DEM are equivalent to 50 mg and 75 mg of its free base, respectively.

Figure 5:
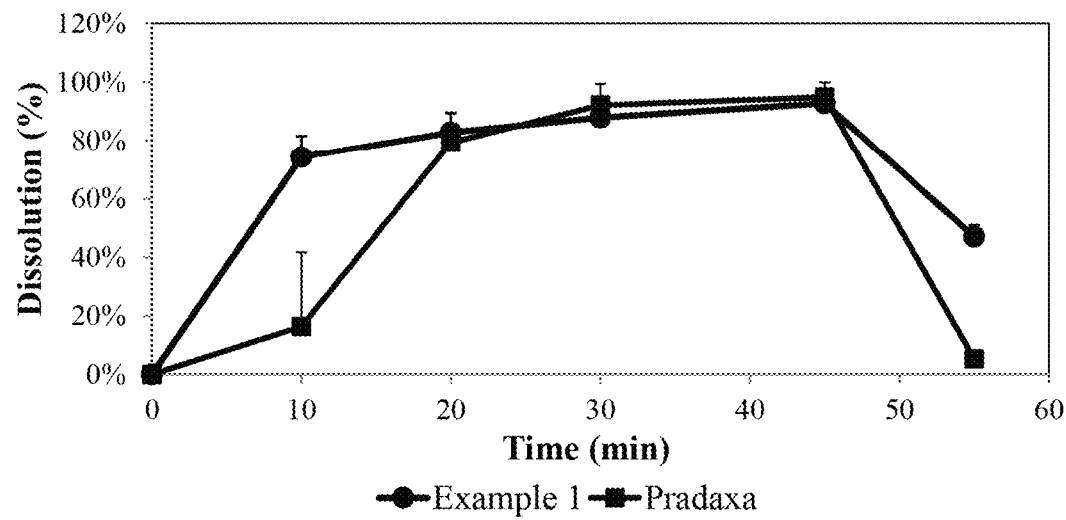
FIG. 5 is the dissolution profile of the granules described in Example 1.

A two-stage method with 45 minutes at the gastric phase (pH 2.0) and 10 minutes at the intestinal phase (pH 6.8) was used to measure the dissolution profile of the fill formulation. As shown in FIG. 5, compared with the commercial product Pradaxa®, the fill formulation in this example showed a more rapid dissolution at low pH and less precipitation at pH 6.8. The error bars represented the standard deviation of n=3.

EXAMPLE 2

In this example, a DEM comprising granular formulation was prepared by a hot melt granulation process. The compositions of the hot melt DEM formulation were listed in the Table 2.

TABLE 2

The compositions of hot melt DEM formulation

| Compositions | wt % | mg/piece (50 mg dose) | mg/piece, (75 mg dose) |
|---|---|---|---|
| Dabigatran etexilate mesylate (DEM) | 17.2 | 57.7 | 86.5 |
| Soluplus ® | 35.7 | 120.0 | 180.0 |
| Mannitol | 17.9 | 60.0 | 90.0 |
| Kolliphor P188 | 19.0 | 64.0 | 96.0 |
| Cross-linked carboxymethylcellulose sodium | 9.7 | 32.7 | 49.1 |
| Magnesium stearate | 0.5 | 1.7 | 2.5 |
| Total content | 100.0 | 336.1 | 504.1 |

*57.7 mg and 86.5 mg DEM are equivalent to 50 mg and 75 mg of its free base, respectively.

The hot melt granulation process is briefly described as follows. First, Soluplus® was ground and passed through an 80-mesh sieve, and Kolliphor P188 was ground and passed through a 40-mesh sieve, and then the sieved Soluplus® powder was mixed with other excipients except magnesium stearate in a high-shear granulator with a thermal jacket at the temperature of 65-75° C. until formation of consistent and homogeneous granules were formed. Next, the hot melt granules were passed through a 20-mesh sieve and then blended with magnesium stearate.

Figure 6:
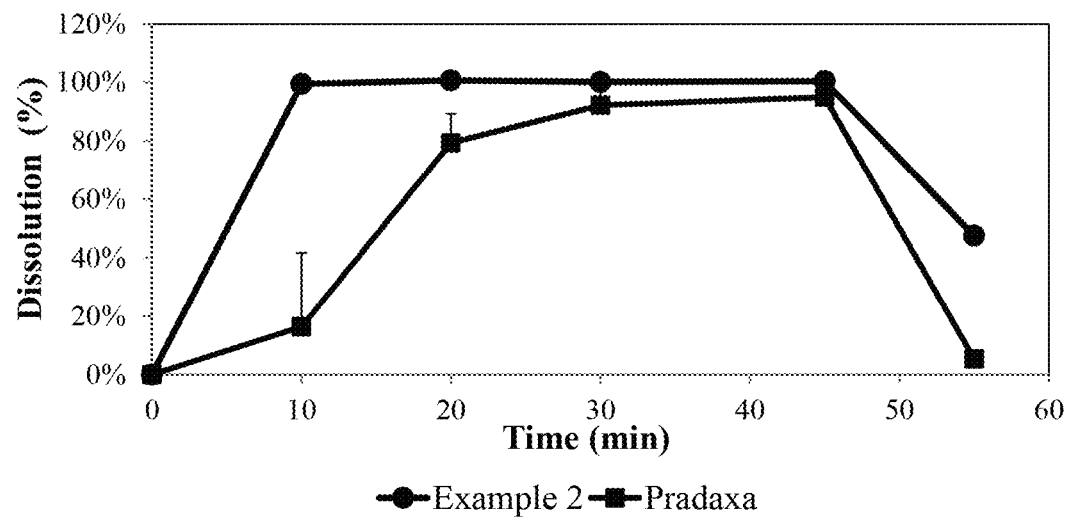
FIG. 6 is the dissolution profile of the multi-particulates described in Example 2.

The hot melt DEM granular preparations (336.1 mg for 50 mg dose, 504.1 mg for 75 mg dose) were filled into the inwardly crimped first opening 2 end of the tubular member through the second opening 3 end. Finally, the filled tubular member was enclosed by a device cap and wrapped in an aluminum pouch (not shown in figures). A two-stage method, 45 mins at the gastric stage (pH 2.0) followed by the intestinal stage (pH 6.8), was used to measure the dissolution profile of the fill formulation. As shown in FIG. 6, compared with Pradaxa®, the fill formulation in this example showed significantly faster dissolution at acidic pH and much less precipitation at the neutral pH. The error bars represent the standard deviation of n=3.

EXAMPLE 3

In this example, a fill formulation was composed of immediate-release levodopa/carbidopa granules and levodopa extended-release multi-particulates. The compositions of the fill formulation were listed in Table 3. The immediate-release granules were prepared by conventional wet granulation process, and extended-release multi-particulates were prepared by extrusion/spheronization/spray coating process. The coating level of the extended-release multi-particulates was 5.1% by weight, with 90% of levodopa released at approximately 3.9 hours.

TABLE 3

The compositions of the levodopa/carbidopa formulation in Example 3

| Compositions | wt % | mg/piece |
|---|---|---|
| Immediate-release granules | | |
| Levodopa | 42.3 | 50.0 |
| Carbidopa monohydrate* | 45.7 | 54.0 |
| Sodium dodecyl sulfate | 1.9 | 2.4 |
| Hydroxypropyl methylcellulose (HPMC) E5 | 4.8 | 5.6 |
| Cross-linked carboxymethylcellulose sodium | 4.8 | 5.6 |
| Magnesium stearate | 0.5 | 0.6 |
| Total content | 100.0 | 118.2 |
| Extended-release multi-particulates | | |
| Levodopa | 70.41 | 200.0 |
| Microcrystalline cellulose | 19.03 | 54.1 |
| Sodium dodecyl sulfate | 3.81 | 10.8 |
| Povidone K29/32 | 1.90 | 5.4 |
| Cellulose acetate 39.8 | 4.12 | 11.7 |
| Copovidon (Kollidone VA64) | 0.73 | 2.1 |
| Total content | 100.00 | 284.1 |

*54 mg of carbidopa monohydrate is equivalent to 50 mg of carbidopa.

EXAMPLE 4

Under the coating level of 7.7% and 10.9% instead of 5.1%, the preparation process and fill formulation of the extended-release multi-particulates in Example 3 were repeated in this example, with 90% of levodopa released at approximately 6.6 hours and 9.3 hours, respectively.

EXAMPLE 5

In this example, the extended-release multi-particulates described in Examples 3 and 4 were coated with conventional enteric-soluble compositions in the art at a coating level of 3-10%.

EXAMPLE 6

In this example, the fill formulation was in the form of granules comprising montelukast sodium, mannitol, hydroxypropyl cellulose and magnesium stearate. The immediate-release granules were prepared by a wet granulation process using a high-shear granulator.

The compositions of the fill formulation were listed in Table 4.

TABLE 4

The compositions of montelukast fill formulation

| Compositions | mg/piece | wt % |
|---|---|---|
| Montelukast sodium * | 4.2 | 0.83 |
| Mannitol | 468.4 | 93.67 |
| Hydroxypropyl cellulose | 25.0 | 5.00 |
| Magnesium stearate | 2.5 | 0.50 |
| Total content | 500.0 | 100.00 |

* 4.2 mg of montelukast sodium is equivalent to 4 mg of montelukast.

The montelukast granular formulations (500 mg) were filled into the inwardly crimped first opening 2 end of the tubular member through the second opening 3 end. Finally, the filled tubular member was enclosed by a device cap and wrapped with an aluminum pouch (not shown in figures).

Montelukast sodium in the fill formulation can be rapidly dissolved in an aqueous medium, with 85% of the drug dissolved in less than 30 minutes.

EXAMPLE 7

In this example, the procedures of Example 6 were repeated for providing a same fill formulation. In this example, the filling weight was 625 mg instead. Each filled device comprised 5 mg of montelukast.

EXAMPLE 8

In this example, the procedures of Example 6 were repeated for providing a same fill formulation. In this example, the filling weight was 1250 mg instead. Each filled device comprised 10 mg of montelukast.

EXAMPLE 9

In this example, the procedures of Example 6 were repeated for providing a fill formulation, the compositions of which were listed in Table 5. In this example, the fill weight was 500 mg. Each filled device comprised 10 mg of montelukast.

TABLE 5

The compositions of montelukast formulation in Example 9

| Compositions | mg/piece | wt % |
|---|---|---|
| Montelukast sodium * | 10.4 | 2.08 |
| Mannitol | 462.1 | 92.42 |
| Hydroxypropyl cellulose | 25.0 | 5.00 |
| Magnesium stearate | 2.5 | 0.50 |
| Total content | 500.0 | 100.00 |

* 10.4 mg of montelukast sodium is equivalent to 10 mg of montelukast.

EXAMPLE 10

In this example, the filler was composed of three formulations, the first being lansoprazole delayed-release multi-particulates, the second being amoxicillin granules, and the third being clarithromycin granules. The compositions of the filler were listed in Table 6. In this example, the fill weight of lansoprazole delayed-release multi-particulates, amoxicillin granules, and clarithromycin granules was 480 mg, 1334 mg, and 840 mg, respectively. Each filled device comprises 30 mg of lansoprazole, 1000 mg of amoxicillin and 500 mg of clarithromycin.

TABLE 6

The compositions of the fill formulation in Example 10

| Compositions | mg/piece | wt % |
|---|---|---|
| Lansoprazole delayed-release multi-particulates: | | |
| Core: | | |
| Lansoprazole | 30.0 | 6.3 |
| Sugar pellets | 150.0 | 31.3 |
| Corn starch | 54.0 | 11.3 |
| Sucrose | 58.0 | 12.1 |
| Low-substituted hydroxypropyl cellulose | 54.0 | 11.3 |
| Hydroxypropyl cellulose | 4.0 | 0.8 |
| Magnesium carbonate | 30.0 | 6.3 |
| Enteric coating: | | |
| Eudragit L-30D solid component | 62.8 | 13.1 |
| Talcum powder | 19.2 | 4.0 |
| PEG 6000 | 6.4 | 1.3 |
| Tween 80 | 3.2 | 0.7 |
| Titanium dioxide | 8.4 | 1.8 |
| Total content | 480.0 | 100.0 |
| Amoxicillin granules: | | |
| Amoxicillin trihydrate | 1000 | 75.0 |
| Microcrystalline cellulose | 327 | 24.5 |
| Magnesium stearate | 7 | 0.5 |
| Total content | 1334 | 100.0 |
| Clarithromycin granules: | | |
| Clarithromycin | 500 | 59.5 |
| Microcrystalline cellulose | 252 | 30.0 |
| Cross-linked carboxymethylcellulose sodium | 42 | 5.0 |
| Povidone | 42 | 5.0 |
| Magnesium stearate | 4 | 0.5 |
| Total content | 840 | 100.00 |

EXAMPLE 11

In this example, the filler was composed of three formulations, the first being omeprazole delayed-release multi-particulates, the second being amoxicillin granules, and the third being clarithromycin granules. The compositions of the filler were listed in Table 7. In this example, the fill weight of omeprazole delayed-release multi-particulates, amoxicillin granules, and clarithromycin granules is 320 mg, 1334 mg, and 840 mg, respectively. Each filled device included 20 mg of omeprazole, 1000 mg of amoxicillin and 500 mg of clarithromycin.

TABLE 7

The compositions of the fill formulation in Example 11

| Compositions | mg/piece | wt % |
|---|---|---|
| Omeprazole delayed-release multi-particulates: | | |
| Core: | | |
| Omeprazole | 20.0 | 6.3 |
| Sugar pellets | 100.0 | 31.3 |
| Corn starch | 36.0 | 11.3 |
| Sucrose | 38.7 | 12.1 |
| Low-substituted hydroxypropyl cellulose | 36.0 | 11.3 |
| Hydroxypropyl cellulose | 2.7 | 0.8 |
| Magnesium carbonate | 20.0 | 6.3 |
| Enteric coating: | | |
| Eudragit L-30D solid component | 41.9 | 13.1 |
| Talcum powder | 12.8 | 4.0 |
| PEG 6000 | 4.3 | 1.3 |
| Tween 80 | 2.1 | 0.7 |
| Titanium dioxide | 5.6 | 1.8 |
| Total content | 320.0 | 100.0 |
| Amoxicillin granules: | | |
| Amoxicillin trihydrate | 1000 | 75.0 |
| Microcrystalline cellulose | 327 | 24.5 |
| Magnesium stearate | 7 | 0.5 |
| Total content | 1334 | 100.0 |
| Clarithromycin granules: | | |
| Clarithromycin | 500 | 59.5 |
| Microcrystalline cellulose | 252 | 30.0 |
| Cross-linked carboxymethylcellulose sodium | 42 | 5.0 |
| Povidone | 42 | 5.0 |
| Magnesium stearate | 4 | 0.5 |
| Total content | 840 | 100.00 |

EXAMPLE 12

In this example, the fill formulation in the form of granules comprised each individual drug or a combination of the following cold drugs: acetaminophen, dextromethorphan, doxylamine, pseudoephedrine and diphenhydramine. The immediate-release granules can be prepared by a wet granulation process using a high-shear granulator. The dosage ranges of these APIs were listed in Table 8.

TABLE 8

The dosage ranges of the cold drugs in Example 12

| Active pharmaceutical preparation (drug) | Dosage range (mg) |
|---|---|
| Acetaminophen | 250-1000 |
| Dextromethorphan | 10-30 |
| Doxylamine | 6.25-12.5 |
| Pseudoephedrine | 20-30 |
| Diphenhydramine | 12.5-25 |

What is claimed is:

1. An oral drug delivery device comprising a tubular member, a drug holding part, a device cap and a turbulence-creating means, wherein the tubular member has openings at both ends and an inner cavity with a first opening at one end and a second opening at the other end, and the inner cavity communicates the first opening and the second opening; the drug holding part has a porous structure, which is retained in the inner cavity near the first opening for holding granules or multi-particulates containing active pharmaceutical ingredients; the porous structure has one or more orifices allowing the passage of liquid, and the orifices has a smaller diameter than the granules or multi-particulates containing the active pharmaceutical ingredients; the device cap is a detachable connection and is disposed outside the second opening; the turbulence-creating means comprises a step structure or a fold structure provided in the inner cavity and positioned between the second opening and the drug holding part;

wherein a cross-sectional diameter of the inner cavity at the fold structure is smaller than that of the inner cavity at a junction of the tubular member and the fold structure, and a minimum cross-sectional diameter of the inner cavity at the fold structure is not less than one-fifth of a cross-sectional diameter of the inner cavity of the tubular member;

wherein the tubular member has at least two tubular segments which are connected to each other hermetically and can be elongated or shorten axially along the tubular member, the tubular segments are connected by the telescopic nesting; when the tubular member is elongated, a turbulence-creating means with at least one step structure is formed.

2. The oral drug delivery device as defined in claim 1, wherein the first opening has a diameter smaller than a minimum diameter of the drug holding part.

3. The oral drug delivery device as defined in claim 1, wherein the number of the tubular segments is 2-5.

4. The oral drug delivery device as defined in claim 3, wherein, the number of the tubular segments is three: in the direction from the first opening to the second opening, the inner diameter of the first tubular segment is the same as the inner diameter of the third tubular segment, and the outer diameter of the second tubular segment is smaller than the inner diameter of the first tubular segment, wherein each tubular segment can be elongated or shorten axially along the other tubular segments; or, the inner diameter of the first tubular segment, the outer diameter of the second tubular segment, the inner diameter of the second tubular segment and the outer diameter of the third tubular segment gradually decrease in the direction from the first opening to the second opening, and each tubular segment can be elongated or shorten axially along the other tubular segments; or the number of the tubular segments is four: in the direction from the first opening to the second opening, the inner diameter of the first tubular segment is the same as the inner diameter of the third tubular segment, and the inner diameter of the second tubular segment is the same as the inner diameter of the fourth tubular segment, wherein the inner diameter of the second tubular segment is smaller than the first tubular segment, and each tubular segment can be elongated or shorten axially along the other tubular segments; or, the inner diameters of the first tubular segment to the fourth tubular segment in the direction from the first opening to the second opening gradually decrease, and each tubular segment can be elongated or shorten axially along the other tubular segments.

5. The oral drug delivery device as defined in claim 1, wherein the tubular member has at least one fold structure with a pair of wing parts and a turning end; the fold structure can be elongated or shorten axially along the tubular member, and forming a turbulence-creating means when the tubular member is elongated.

6. The oral drug delivery device as defined in claim 5, wherein a plurality of successive fold structures forms a fold cluster configuration having a number of 1-5.

7. The oral drug delivery device as defined in claim 1, wherein the tubular member has a maximum outer diameter of 4.0-15.0 mm and a minimum inner diameter of 2.0-14.8 mm, and the length of the tubular member is 5-30 cm in a shorten form and 10-50 cm in an elongated form.

8. The oral drug delivery device as defined in claim 1, when the drug holding part comprises granules or multi-particulates containing active pharmaceutical ingredients, the granules or multi-particulates has a diameter of 50-5000 µm; the active pharmaceutical ingredients contained in the granules or multi-particulates include, but are not limited to one or more of the following: dabigatran etexilate or pharmaceutically acceptable salt thereof, levodopa/carbidopa, montelukast, lansoprazole, omeprazole, amoxicillin, clarithromycin, acetaminophen, dextromethorphan, doxylamine, pseudoephedrine and diphenhydramine.

9. A method for preparing the oral drug delivery device as defined in claim 1, comprising the following steps:
1) preparing the turbulence-creating means and assembling it with the tubular member;
2) preparing the drug holding part and retaining it in the inner cavity near the first opening;
3) setting the device cap at the second opening.

10. The oral drug delivery device as defined in claim 2, wherein the second opening has a diameter smaller than the maximum diameter of the drug holding part.

11. The oral drug delivery device as defined in claim 3, wherein the number of the tubular segments is 2-4.

12. The oral drug delivery device as defined in claim 11, wherein the number of the tubular segments is 3.

13. The oral drug delivery device as defined in claim 6, wherein a plurality of successive fold structures forms a fold cluster configuration having a number of 2-3.

14. The oral drug delivery device as defined in claim 8, wherein the granules or multi-particulates has a diameter of 75-2000 µm.

15. The oral drug delivery device as defined in claim 13, wherein the granules or multi-particulates has a diameter of 100-1000 µm.

16. The method for preparing the oral drug delivery device as defined in claim 9, wherein the step of filling the drug is further included before the step 3).

17. A method for promoting the drug swallowing of a patient in need by using the oral drug delivery device as defined in claim 1, wherein the device cap is removed from the second opening prior to use; the first opening end is in contact with drinkable liquids; the second opening end is placed in the patient's mouth; wherein the tubular member allows the passage of the drinkable liquids and create turbulence; the drug holding part is located inside the tubular member near the first opening end to retain the drug in the form of granules or multi-particulates.

18. The method as defined in claim 17, wherein, when the drug holding part comprises granules or multi-particulates containing active pharmaceutical ingredients, the granules or multi-particulates has a diameter of 50-5000 µm; the active pharmaceutical ingredients contained in the granules or multi-particulates include, but are not limited to one or more of the following: dabigatran etexilate or pharmaceutically acceptable salt thereof, levodopa/carbidopa, montelukast, lansoprazole, omeprazole, amoxicillin, clarithromycin, acetaminophen, dextromethorphan, doxylamine, pseudoephedrine and diphenhydramine.

19. The oral drug delivery device as defined in claim 1, the turbulence-creating means is the step structure provided in the inner cavity and positioned between the second opening and the drug holding part;
   wherein the tubular member has at least two tubular segments which are connected to each other hermetically and can be elongated or shorten axially along the tubular member, the tubular segments are connected by the telescopic nesting; when the tubular member is elongated, a turbulence-creating means with at least one step structure is formed.

* * * * *